Figure 1:
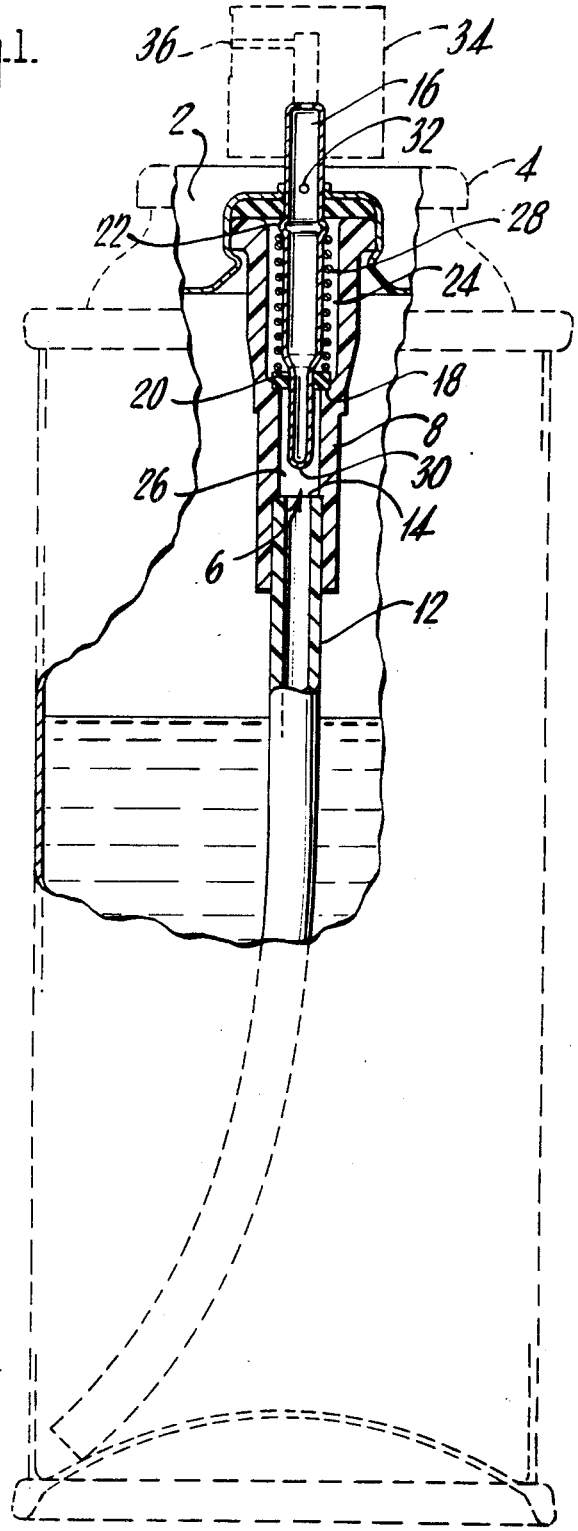

United States Defensive Publication [19] (H) [11] T106,202

Mackles [43] Mar. 4, 1986

[54] HIGH CONCENTRATION METERED AEROSOL ANTIPERSPIRANT PRODUCT

[76] Inventor: Leonard Mackles, 311 E. 23rd St., New York, N.Y. 10010

[21] Appl. No.: 537,541

[22] Filed: Sep. 30, 1983

Related U.S. Application Data

[63] Continuation of Ser. No. 23,808, Mar. 26, 1979, abandoned.

[51] Int. Cl.[4] ..... A61K 9/14

[52] U.S. Cl. ..... 424/46; 424/47

[57] ABSTRACT

An article of manufacture comprising a metered aerosol container having incorporated therein an antiperspirant material, in high concentration suspended in an oily vehicle and containing relatively low levels of propellant.

14 Claims, No Sheets Drawing,

26 Pages Specification

The file of this unexamined application may be inspected and copies thereof may be purchased (849 O.G. 1221, Apr. 9, 1968).